United States Patent [19]

Terashima et al.

[11] Patent Number: 5,653,942
[45] Date of Patent: Aug. 5, 1997

[54] CHEMICAL ANALYSIS ELEMENT CARTRIDGE

[75] Inventors: Kaoru Terashima; Shigeru Tezuka, both of Saitama-ken, Japan

[73] Assignee: Fuji Photo Film Co., Ltd., Kanagawa-ken, Japan

[21] Appl. No.: 443,479

[22] Filed: May 18, 1995

[30] Foreign Application Priority Data

May 18, 1994 [JP] Japan .................. 6-103887

[51] Int. Cl.⁶ ..................................... G01N 35/00
[52] U.S. Cl. .................. 422/63; 422/58; 422/104; 436/43; 436/46; 221/198
[58] Field of Search ................. 422/58, 63, 66, 422/68.1, 99, 102, 104; 436/43, 44, 46, 47, 48, 49; 221/197, 198

[56] References Cited

U.S. PATENT DOCUMENTS

| | | | |
|---|---|---|---|
| Re. 30,595 | 4/1981 | Covington et al. | 422/63 |
| 4,190,420 | 2/1980 | Covington et al. | 422/63 |
| 4,279,861 | 7/1981 | Jessop | 422/67 |
| 4,512,952 | 4/1985 | Blanding et al. | 422/63 |
| 5,030,418 | 7/1991 | Miyata | 422/63 |

*Primary Examiner*—Long V. Le
*Attorney, Agent, or Firm*—McAulay Fisher Nissen Goldberg & Kiel, LLP

[57] ABSTRACT

A chemical analysis slide cartridge includes a box-like cartridge body in which a plurality of chemical analysis slides are stacked. A slide take-out port is formed in one end of the cartridge body and the chemical analysis slides in the cartridge body are taken out one by one through the take-out port. A pressing member is slidably received in the cartridge body and is adapted to be brought into contact with the stack of the slides on the side remote from the take-out port to push the stack of the slides toward the take-out port. Ratchet teeth are formed on the inner wall of the cartridge body and a claw adapted to be engaged with the ratchet teeth is formed on the pressing member. The ratchet teeth are not formed in a predetermined area near the end of the cartridge body remote from the take-out port so that the claw cannot be engaged with the ratchet teeth when the pressing member is near the end of the cartridge body remote from the take-out port.

4 Claims, 3 Drawing Sheets

CHEMICAL ANALYSIS ELEMENT CARTRIDGE

BACKGROUND OF THE INVENTION

1. Field of the Invention

This invention relates to a chemical analysis element cartridge for storing a plurality of chemical analysis elements such as those for quantitatively analyzing the content of a specific chemical component contained in a sample liquid such as blood or urine or those for quantitatively analyzing the activity of particular ionic substances contained in a sample liquid such as blood or urine.

2. Description of the Prior Art

There have been put into practice various "dry-to-the-touch" chemical analysis elements. For example, there has been proposed, for instance, in U.S. Pat. Nos. 3,992,158; 4,292,272 and 5,019,347 and European Patent 0 162 302B and put into practice a "dry-to-the-touch" chemical analysis film with which the content or the concentration of a specific chemical component contained in a sample liquid, the activity thereof or the content of a solid component can be quantitatively analyzed by only spotting a droplet of the sample liquid on the film. As such a dry chemical analysis film, there has been known an integrated multi-layered chemical analysis film (sometimes referred to as "multi-layered chemical analysis element") comprising a support sheet of organic polymer and a reagent layer formed on the support sheet. The reagent layer contains therein a reagent whose optical density changes by chemical reaction, biochemical reaction, immunoreaction or the like with a specific biochemical component contained in the sample liquid. A spreading layer is sometimes formed over the reagent layer. Further a dry chemical analysis film which is formed of filter paper and has one or more layers has been proposed, for instance, in U.S. Pat. No. 4,477,575, and partly put into practice.

The chemical analysis film is generally in the form of a film chip of a predetermined shape such as square or rectangle. In the past, the film chip is generally provided with a frame of organic polymer or the like for facilitating automated handling of the film chip. The film chip provided with such a frame is generally called a chemical analysis slide. However in a chemical analysis apparatus we have previously proposed, the chemical analysis film chip is used as it is without frame. The chemical analysis film without frame is generally referred to as "a frameless chemical analysis film".

Further there has been proposed, for instance, in U.S. Pat. Nos. 4,053,381 and 4,437,970 and put into practice a "dry-to-the-touch" electrolyte analysis slide for quantitatively analyzing the activity of particular ionic substances contained in a sample liquid such as blood or urine in a potentiometric way. The electrolyte analysis slide is a kind of electrochemical sensors and comprises a pair of ion-selective (or ion-specific) electrodes.

In this specification, the term "chemical analysis element" should be broadly interpreted to include the chemical analysis slide, the frameless chemical analysis film, the single-layered or multi-layered chemical analysis film formed of filter paper (with or without frame), and the electrolyte analysis slide described above.

For instance, in Japanese Utility Model Publication No. 57(1982)-53271 (U.S. Pat. No. 4,151,931), there is disclosed a chemical analysis element cartridge in which a plurality of the chemical analysis elements are stacked and from which the chemical analysis elements are taken out one by one. In the cartridge, a plurality of chemical analysis elements are stacked in a cartridge body which is provided with an element take-out port in a side surface of the upper portion thereof and the uppermost element is pushed out and fed to a chemical analysis apparatus through the element take-out port by a pusher blade which is moved in a horizontal direction. The stack of the elements are supported on a pressing member which is disposed in the cartridge body and is permitted to move only upward by a ratchet mechanism. The pressing member is lifted upward by a plunger inserted into the cartridge body from below so that the stack of the elements is moved upward by a distance equal to the thickness of one element and the second uppermost element is brought to the element take-out port each time the uppermost element is pushed out.

However this cartridge is disadvantageous in the following point. That is, when the cartridge falls or is subjected to an impact by accident during transfer or storing, an excessive pressure can act on the chemical analysis elements stored therein or the pressing member can be damaged, whereby take-out of the chemical analysis elements or measurement can be adversely affected. This problem is especially serious in the case of a cartridge storing therein chemical analysis elements such as electrolyte analysis slides which are relatively large in weight.

More particularly, in the aforesaid chemical analysis element cartridge where a pressing member having a ratchet mechanism is urged by a plunger, the ratchet mechanism permits the pressing member to be moved by a weak force in the direction of pushing the stack of the elements but does not permit the pressing member to be moved in the reverse direction. Accordingly when the cartridge falls with the element take-out port down, the stack of the elements is compressed toward the take-out port and the pressing member moves toward the take-out port and is locked there, whereby the stack of the elements is kept compressed and it can become impossible to take out the elements due to an excessively large pressure acting on the stack of the elements.

On the other hand when the cartridge falls with the end of the cartridge remote from the take-out port directed downward, the weight of the elements totally acts on the ratchet mechanism to damage the ratchet teeth and/or the ratchet claws, whereby it can become impossible to hold the uppermost element at the height of the take-out port, which gives rise to problem in taking out the element. For example assuming that the impact acting on the cartridge when it falls one meter is 1200G and the weight of fifty elements stored in the cartridge is 50 g, a force of 60 Kg acts on the pressing member. It is difficult for the ratchet claws to support such a large force.

SUMMARY OF THE INVENTION

In view of the foregoing observations and description, the primary object of the present invention is to provide a chemical analysis element cartridge in which the stack of the chemical analysis elements stored in the cartridge can be prevented from being compressed and the pressing member can be prevented from being damaged even if an impact acts on the cartridge, for instance, when the cartridge falls.

The chemical analysis element cartridge in accordance with the present invention comprises a box-like cartridge body in which a plurality of chemical analysis elements are stacked, an element take-out port which is formed in one end of the cartridge body and through which the chemical analysis elements in the cartridge body are taken out one by one, a pressing member which is slidably received in the cartridge body and is adapted to be brought into contact with the stack of the elements on the side remote from the take-out port to push the stack of the elements toward the take-out port and an engagement mechanism which permits the pressing member to move toward the take-out port but does not permit the pressing member to move away from the take-out port, and is characterized in that the engagement mechanism is arranged so that the engagement mechanism does not engage and permits the pressing member to move away from the take-out port in an initial state where a predetermined number of chemical analysis elements are stacked in the cartridge body.

The engagement mechanism may comprise ratchet teeth formed on the inner wall of the cartridge body and a claw which is formed on the pressing member and is adapted to be engaged with the ratchet teeth. In this case, the ratchet teeth are not formed in a predetermined area near the end of the cartridge body remote from the take-out port so that the claw cannot be engaged with the ratchet teeth when the pressing member is near the end of the cartridge body remote from the take-out port.

The length d of the area in which the ratchet teeth are not formed may be about 20 to about 50% of the length of the shortest side of the chemical analysis element. For example when the chemical analysis element is 28 mm×24 mm in size, the length d is in the range of about 5.0 mm to about 12 mm. The area may be of such a length that the engagement mechanism does not engage until one or several (3 to 5) chemical analysis elements are taken out from the cartridge. The area of such a length is economically advantageous in that the chemical analysis elements of different thicknesses (the thickness of the chemical analysis elements can differ from element to element due to manufacturing error or can differ according to the analyte or the component to be analyzed) can be stored in the cartridges of the same size.

Accordingly in the initial state where the predetermined number of chemical analysis elements are in the cartridge, the pressing member cannot be locked in a position where the stack of the elements is kept compressed even if the cartridge falls with the element take-out port down and the stack of the elements is once compressed toward the take-out port since the engagement mechanism cannot engage in the initial state and accordingly the pressing member once moved toward the take-out port is returned to the original position under the restoring force of the stack of the chemical analysis elements. Further even if the cartridge falls with the end of the cartridge remote from the take-out port directed downward and a heavy load acts on the pressing member, the load does not act on the engagement mechanism and is supported by movement of the pressing member toward the take-out port, and accordingly the engagement mechanism cannot be damaged.

DESCRIPTION OF THE PREFERRED EMBODIMENT

Figure 1:
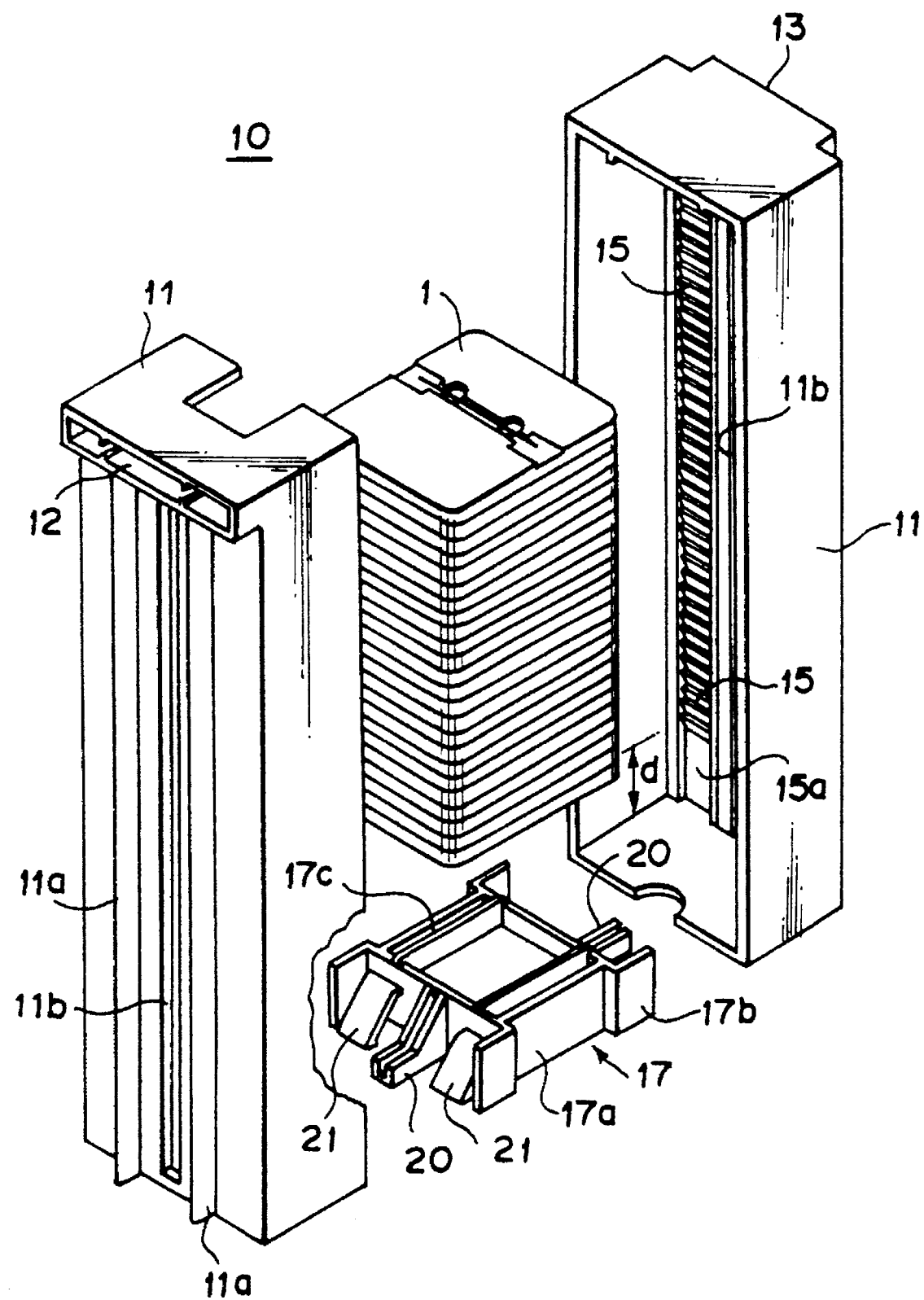
FIG. 1 is an exploded perspective view of a chemical analysis element cartridge in accordance with an embodiment of the present invention.

As shown in FIG. 1, a chemical analysis slide cartridge 10 in accordance with an embodiment of the present invention comprises a box-like cartridge body 11 in which a plurality of chemical analysis slides 1 are stored in a stack. The cartridge body 11 is a rectangular column in shape and is formed by mating together left and right halves along a vertical plane at the center thereof. A chemical analysis slide take-out port 12 is formed in one side wall of the cartridge body 11 near the top wall thereof. The take-out port 12 is in the form of a slit open in said one side wall and has such a width that one chemical analysis slide 1 can pass therethrough, and an opening 13 through which a pusher blade 30 (FIG. 2) is inserted into the cartridge body 11 is formed in the side wall opposite to said one side wall.

A pair of outer ribs 11a are formed on each of the left and right side walls of the cartridge body 11. The space between the outer ribs 11a on the left side wall differs from that on the right side wall to prevent insertion of the cartridge 10 into, for instance, a slider or film supplier (not shown) of a chemical analysis apparatus in a wrong position.

Figure 3:
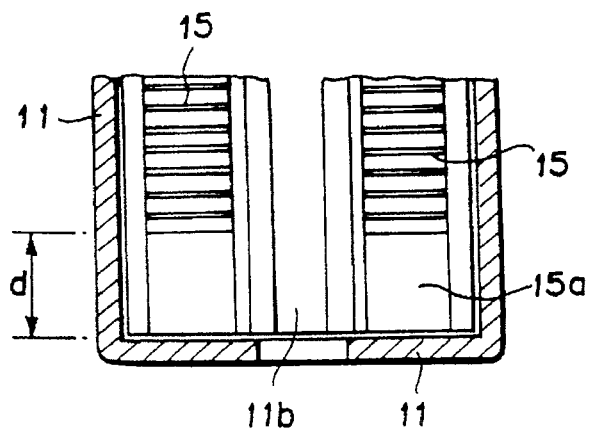
FIG. 3 is a fragmentary cross-sectional view of the cartridge body taken along line A—A in FIG. 2.
Figure 4:
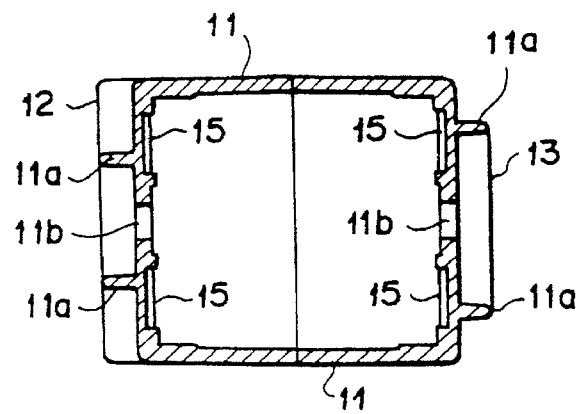
FIG. 4 is a cross-sectional view taken along line B—B in FIG. 2.

In each of the left and right side walls, a longitudinal slit 11b (See also FIGS. 3 and 4) is formed to extend in the longitudinal direction of the cartridge body 11 between the outer ribs 11a. Ratchet teeth 15 are formed on the inner surface of each of the left and right side walls to extend upward along the slit 11b on opposite sides thereof from a position at a distance of d from the bottom of the cartridge body 11. The portion 15a below the ratchet teeth 15 is in flush with the base of the ratchet teeth 15.

A pressing member 17 which supports the stack of the slides 1 and an engagement mechanism 18 which holds the pressing member 17 so that the uppermost slide in the stack of the slides 1 supported on the pressing member 17 is constantly held in a predetermined position with respect to the take-out port 12 are received in the cartridge body 11. The pressing member 17 is provided with a projections 20 for urging upward the pressing member 17 and ratchet claws 21 which form the engagement mechanism 18 together with the ratchet teeth 15.

Figure 5:
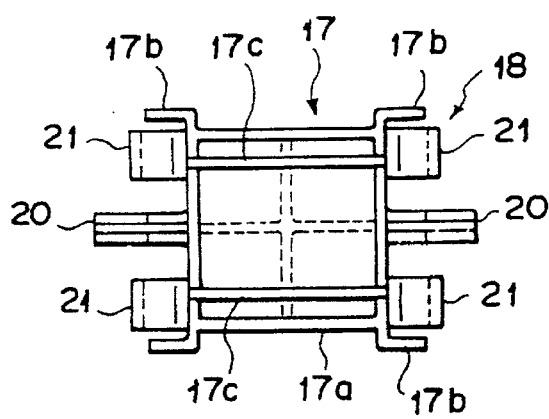
FIG. 5 is a plan view of the pressing member.

As clearly shown in FIG. 5, the pressing member 17 comprises a substantially rectangular body portion 17a and sliding portions 17b formed on the body portion 17a at the respective corners thereof. The sliding portions 17b slide on the inner surfaces of the corners of the cartridge body 11. The body portion 17a comprises an outer frame and a plate member provided in the outer frame. A cross reinforcement is provided on the bottom of the plate member and a pair of pressing portions 17c are provided on the plate member near opposite sides of the body portion 17a. The pressing portions 17c are brought into contact with edge portions of the chemical analysis slide 1 outside the measuring area of the slide.

Said projections 20 are formed integrally with the side walls of the body portion 17a to laterally extend from the respective side walls at the middle thereof. Each of the projections 20 extends outward through the vertical slit 11b to a position short of the outer surface of the ribs 11a. A feed means 31 shown by chained line in FIG. 2 pushes upward the projections 20 to urge upward the pressing member 17.

Figure 2:
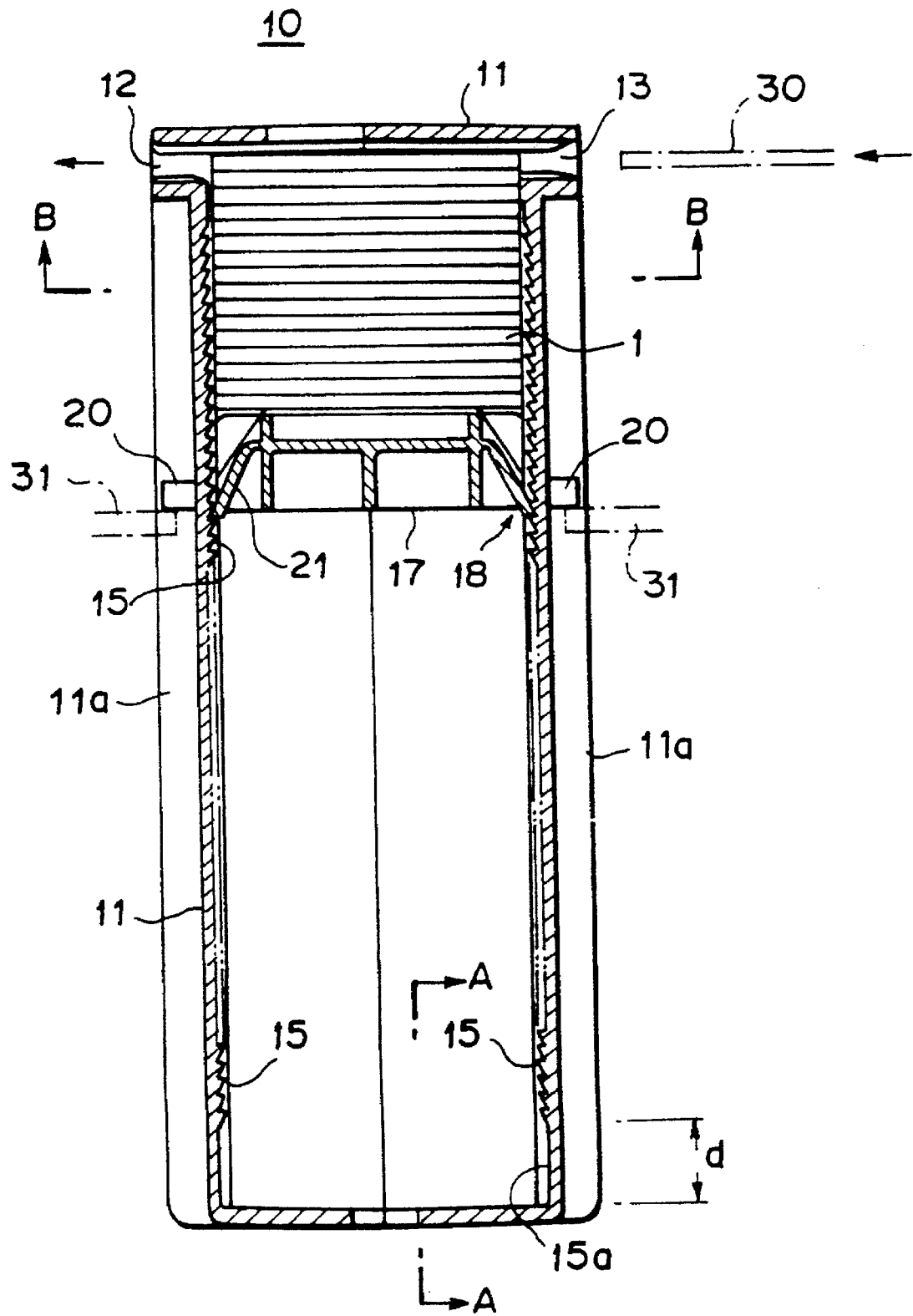
FIG. 2 is a cross-sectional view showing the cartridge in use.

A pair of claws 21 are formed integrally with the pressing member 17 to extend outwardly downwardly (as seen in FIGS. 1 and 2) from each of the left and right side walls of the pressing member 17 on opposite sides of the projection 20. Each of the claws 21 resiliently abuts against the ratchet teeth 15 at the free end thereof (when the pressing member 17 is above the portion 15a as shown in FIG. 2) so that the free end is engaged with one of the ratchet teeth 15 to prevent downward movement of the pressing member 17 and to permit upward movement of the same.

The chemical analysis slides 1 stored in the cartridge 10 are, for instance, electrolyte analysis slides each of which is provided with a plastic frame covering the edge portions outside the measuring area and is like a flat slide. The length d of the portion 15a where no ratchet tooth is formed is set depending on the total thickness of a predetermined number (e.g., 50) of the slides which are initially stacked in the cartridge 10.

Figure 6:
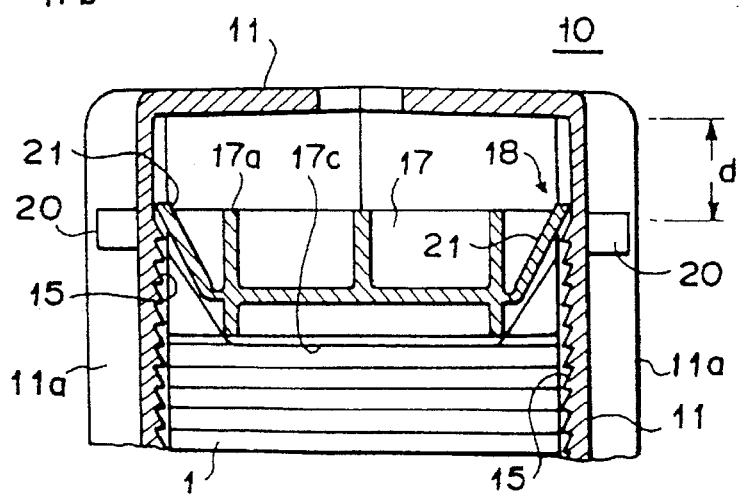
FIG. 6 is a fragmentary cross-sectional view of the cartridge in the initial state with the cartridge body inverted relative to the position shown in FIG. 1.

FIG. 6 shows the initial state of the cartridge 10. In FIG. 6, the cartridge is inverted.

In the initial state, the pressing member 17 is near the end of the cartridge body 11 remote from the take-out port 12 and the claws 21 of the pressing member 17 are free, and accordingly the pressing member 17 is freely movable within the length of d (in the range corresponding to the portion 15a).

The cartridge 10 is transferred or handled, for instance, to be loaded in a chemical analysis slide supplier of a chemical analysis apparatus in the state shown in FIG. 6. Accordingly, when the cartridge 10 falls with the take-out port 12 down by accident, the claws 21 of the pressing member 17 cannot be brought into engagement with the ratchet teeth 15 though the pressing member 17 moves toward the take-out port 12 and compresses the stack of the slides 1. Thereafter the pressing member 17 returns to the original position under the restoring force of the stack of the elements 1.

When the cartridge 10 falls with the end of the cartridge remote from the take-out port 12 directed downward, the pressing member 17 moves toward the end of the cartridge remote from the take-out port 12 since the claws 21 are not in engagement with the ratchet teeth 15. However load of the pressing member 17 is supported by the bottom of the cartridge body 11 and since both the pressing member 17 and the cartridge body 11 are sufficient in strength, they cannot be damaged.

Further even if the pressing member 17 moves to abut against the bottom of the cartridge body 11, the space formed between the stack of the slides 1 and the pressing member 17 by the movement of the pressing member 17 is not sufficient to permit a slide 1 to erect or to turn upside down. Accordingly the slides 1 can be orderly fed toward the take-out port 12. When the slides 1 are fed to the chemical analysis apparatus, the pressing member 17 is pushed upward by way of the engagement between the projections 20 and the feeding means 31 up to a position where the uppermost slide is opposed to the take-out port 12. This step is repeated each time one slide is pushed out.

The length d of the portion 15a, where no ratchet tooth is formed, is set taking into account the height of the stack of the slides 1 and the distance between the upper surface of the pressing member 17 and the engaging point of the claws 21 with respect to the inner height of the cartridge body 11 so that the claws 21 of the pressing member 17 cannot be engaged with the ratchet teeth 15 so long as a predetermined number of the slides 1 are in the cartridge body 11. Since the thickness of the slide 1 can differ from slide to slide due to manufacturing errors and the difference in the thickness is multiplied by the number of the slides stacked, the length d should be set so that the claws 21 of the pressing member 17 cannot be engaged with the ratchet teeth 15 even for the smallest possible height of the stack of the slides 1.

EXAMPLE

A chemical analysis element cartridge 10 having the structure shown in FIGS. 1 to 6 was made of a blend of high-impact polystyrene (70%) and general-purpose polystyrene (30%) and fifty dry analysis slides for quantitatively analyzing electrolytes ($Na^+$, $K^+$, $Cl^-$) each being 28 mm×24 mm in size and 1.65 mm in thickness were stacked in the cartridge 10. The total weight of the fifty dry analysis slides was about 50 g. In the cartridge, the length d of the portion 15a where no ratchet tooth was formed was set to 8.0 mm taking into account the fluctuation in thickness of the slides due to manufacturing errors and the difference in the thickness according to the kind of the slides.

The cartridge was dropped about 50 cm to a wooden floor with the end remote from the take-out port 12 directed downward and with the take-out port 12 directed downward. The claws 21 were not brought into engagement with the ratchet teeth 15 and the stack of the slides did not come to be kept compressed by the pressing member 17. Further the slides were kept stacked in order. Further none of the cartridge body 11, claws 21 of the pressing member 17 and the ratchet teeth 15 (especially those adjacent to the portion 15a where no ratchet tooth is formed) was damaged. After the drop test, the cartridge 10 was loaded in a chemical analysis apparatus and the chemical analysis slides in the cartridge were taken out. The chemical analysis slides could be successfully taken out.

The chemical analysis element cartridge of the present invention can be applied to various chemical analysis elements without being limited to the electrolyte analysis slide which is hard, flat and relatively thick. For example, the cartridge of the present invention can also be applied to a chemical analysis slide, a frameless chemical analysis film, a chemical analysis film chip laminated with a protective substrate, the single-layered or multi-layered chemical analysis film formed of filter paper (with or without frame), and the like.

Though, in the embodiment described above, the claws 21 of the engagement mechanism 18 and the projections 20 of the pressing member 17 are separately formed, the claws 21 and the projections 20 may be formed integrally with each other into a unit which, for instance, is arranged to abut against the pressing member from below. Further, though, in the embodiment described above, the pressing member 17 is urged toward the take-out port 12 by the feeding means which acts on the ends of the projections 21 projecting outside the cartridge body 11 through the slits, the pressing member 17 may be urged toward the take-out port 12 by a feeding means which is inserted into the cartridge body 11 and directly acts on the pressing member 17. In this case, the projections 20 need not project outside the cartridge body 11, and may be omitted depending on the structure of the pressing member 17.

What is claimed is:

1. A chemical analysis element cartridge comprising a cartridge body in which a plurality of chemical analysis elements are stacked, an element take-out port which is formed in one end of the cartridge body and through which the chemical analysis elements in the cartridge body are taken out one by one, a pressing member which is slidably received in the cartridge body and is adapted to be brought into contact with the stack of the elements on a side remote from the take-out port to push the stack of the elements toward the take-out port and an engagement mechanism which permits the pressing member to move toward the take-out port but does not permit the pressing member to move away from the take-out port, wherein the improvement comprises that the engagement mechanism is arranged so that the engagement mechanism does not engage and permits the pressing member to move away from the take-out port in an initial state where a predetermined initial full number of chemical analysis elements are stacked in the cartridge body.

2. A chemical analysis element cartridge as defined in claim 1 in which said engagement mechanism comprises ratchet teeth formed on an inner wall of the cartridge body and a claw which is formed on the pressing member and is adapted to be engaged with the ratchet teeth, the ratchet teeth being not formed in a predetermined area near an end of the cartridge body remote from the take-out port so that the claw cannot be engaged with the ratchet teeth when the pressing member is near the end of the cartridge body remote from the take-out port.

3. A chemical analysis element cartridge, comprising:

a body containing a plurality of chemical analysis elements in a stacked configuration;

an element take-out port which is formed in one end of the cartridge body through which the chemical analysis elements are taken out one by one;

a pressing member slidably received in the cartridge body and adapted to be brought into contact with the stack of the elements on a side remote from the take-out port to push the stack of the elements toward the take-out port; and an engagement mechanism which permits the pressing member to move toward the take-out port but does not permit the pressing member to move away from the take-out port, the engagement mechanism being arranged so that when the body is full of chemical analysis elements, the engagement mechanism does not engage, thus permitting the pressing member to move away from the take-out port.

4. A chemical analysis dement cartridge as defined in claim 3 wherein the engagement mechanism comprises:

ratchet teeth formed along an inner wall of the cartridge body; and a claw formed on the pressing member adapted to engage the ratchet teeth, the ratchet teeth being absent in a predetermined area near an end of the cartridge body opposite the take-out port so that the claw cannot be engaged with the ratchet teeth when the pressing member is near the end of the cartridge body remote from the take-out port.

\* \* \* \* \*